(12) United States Patent  
Lutze et al.

(10) Patent No.: US 6,743,230 B2
(45) Date of Patent: Jun. 1, 2004

(54) BIPOLAR GRASPING INSTRUMENT

(75) Inventors: Theodor Lutze, Balgheim (DE); Rupert Mayenberger, Rielasingen (DE); Christoph Rothweiler, Donaueschingen (DE); Dieter Weisshaupt, Immendingen (DE)

(73) Assignee: Aesculap AG & Co. KG, Tulllingen (DE)

( * ) Notice: Subject to any disclaimer, the term of this patent is extended or adjusted under 35 U.S.C. 154(b) by 133 days.

(21) Appl. No.: 10/199,739

(22) Filed: Jul. 18, 2002

(65) Prior Publication Data

US 2002/0183784 A1 Dec. 5, 2002

Related U.S. Application Data

(63) Continuation of application No. PCT/EP00/11052, filed on Nov. 9, 2000.

(30) Foreign Application Priority Data

Jan. 25, 2000 (DE) ........................................ 100 03 020

(51) Int. Cl.[7] ............................................... A61B 18/18
(52) U.S. Cl. ........................................ 606/51; 606/205
(58) Field of Search ................................. 606/170, 171, 606/51, 52, 91, 92, 45–50, 205–208

(56) References Cited

U.S. PATENT DOCUMENTS

| 5,458,598 A | | 10/1995 | Feinberg et al. |
| 5,797,927 A | * | 8/1998 | Yoon ........................ 606/144 |
| 5,797,941 A | | 8/1998 | Schulze et al. |
| 5,984,938 A | * | 11/1999 | Yoon ........................ 606/170 |
| 5,984,939 A | | 11/1999 | Yoon |

FOREIGN PATENT DOCUMENTS

| DE | 44 21 822 | 10/1995 |
| DE | 200 01 204 | 3/2000 |
| EP | 0 598 348 | 5/1994 |
| WO | 96/05776 | 2/1996 |
| WO | 99/40861 | 8/1999 |

OTHER PUBLICATIONS

Brochure entitled "Tripolar® Cutting Forceps," Circon Corporation, undated.

* cited by examiner

Primary Examiner—Michael Peffley
(74) Attorney, Agent, or Firm—Barry R. Lipsitz; Douglas M. McAllister

(57) ABSTRACT

In a bipolar grasping instrument with two clamping jaws movable relative to each other, electrically isolated from one another and each connectable to a pole of an electric high-frequency voltage source, each of the clamping jaws comprising two clamping elements arranged in spaced relation to one another, forming between them a longitudinal slot and each having a clamping surface, and with a cutting device comprising a cutting element displaceable in the longitudinal slots of the clamping jaws and having a cutting edge, in order to improve the design of the drive mechanism and the operability, it is proposed that the cutting element be arranged in the longitudinal slot of the one clamping jaw such that its cutting edge is contained in the longitudinal slot between the clamping elements of this clamping jaw and does not extend beyond its clamping surfaces in the direction towards the other clamping jaw, and that the clamping elements of this clamping jaw be elastically movable relative to the cutting element opposite to the closing movement of the clamping jaws so far that the cutting edge of the cutting element projects beyond the clamping surfaces.

10 Claims, 4 Drawing Sheets

BIPOLAR GRASPING INSTRUMENT

The present disclosure is a continuation of and relates to the subject matter disclosed in international application No. PCT/EP00/11052 of Nov. 9, 2000, which is incorporated herein by reference in its entirety and for all purposes.

BACKGROUND OF THE INVENTION

The invention relates to a bipolar grasping instrument with two clamping jaws movable relative to each other, electrically isolated from one another and each connectable to a pole of an electric high-frequency voltage source, each of the clamping jaws comprising two clamping elements arranged in spaced relation to one another, forming between them a longitudinal slot and each having a clamping surface, and with a cutting device comprising a cutting element displaceable in the longitudinal slots of the clamping jaws and having a cutting edge.

With bipolar grasping instruments it is possible to coagulate tissue in the grasped area so as to control bleeding in this area.

It is known to coagulate certain areas, for example, in vessels, with such instruments and to then transect the vessels by an incision in this coagulated area, with the risk of bleeding being minimized by the preceding coagulation. This requires two completely separate procedural steps which are usually performed with different instruments, namely, on the one hand, the coagulating with a bipolar grasping instrument, and, on the other hand, the transecting of the coagulated tissue with a cutting device.

Bipolar grasping instruments with an integrated cutting device are also known (company prospectus of CIRCON, TRIPOLAR Cutting Forceps; U.S. Pat. No. 5,458,598). In this instrument, the clamping jaws of the grasping instrument are divided by longitudinal slots into two clamping surfaces arranged adjacent one another, and a cutting element provided with a cutting edge, which transects parts of tissue held between the clamping surfaces after the coagulation, can be pushed into the longitudinal slots in the longitudinal direction of the instrument. In this previously known instrument, different drive mechanisms must be provided for closing the clamping jaws to bring about the coagulation and for advancing the cutting element of the cutting device. This instrument, which is preferably designed as a tubular-shafted instrument, is, therefore, of relatively complicated design, and, in addition, the user of this instrument must operate two separate drive mechanisms in order to first grasp and then transect tissue.

The object of the invention is to so design a bipolar grasping instrument of the generic kind that operation is simplified, in particular, by the user only requiring one actuating mechanism for first grasping and then transecting tissue.

SUMMARY OF THE INVENTION

This object is accomplished with a bipolar grasping instrument of the kind described at the outset, in accordance with the invention, in that the cutting element is arranged in the longitudinal slot of the one clamping jaw such that its cutting edge is contained in the longitudinal slot between the clamping elements of this clamping jaw and does not extend beyond its clamping surfaces in the direction towards the other clamping jaw, and in that the clamping elements of this clamping jaw are elastically movable relative to the cutting element opposite to the closing movement of the clamping jaws so far that the cutting edge of the cutting element projects beyond the clamping surfaces.

Thus, at the start of the closing movement of the clamping jaws, the cutting element is accommodated in the longitudinal slot of the one clamping jaw such that the cutting edge of the cutting element is contained within the longitudinal slot and, therefore, does not become operative. In this case, the instrument operates like a conventional bipolar grasping instrument in which the clamping surfaces are placed against the tissue to be grasped without the cutting element appearing at all. In this part of the closing movement, coagulation can be brought about by applying a high-frequency voltage in the conventional way, and, after the coagulation, the bipolar grasping instrument can also be removed again like a conventional bipolar grasping instrument.

If, on the other hand, the closing movement is continued with this bipolar grasping instrument after the coagulation, the clamping jaws are moved together so forcefully that the clamping elements of the clamping jaw carrying the cutting device are moved elastically opposite to the closing movement of the clamping jaws, and this releases the cutting edge of the cutting device which owing to the elastic displacement of the clamping elements then protrudes beyond the clamping surface. Therefore, the instrument is now a cutting instrument in which the cutting element can reach into the longitudinal slot of the other clamping jaw, thereby transecting the tissue engaged between the clamping jaws. This cutting movement immediately follows the normal closing movement of the clamping jaws. The user only has to actuate one drive mechanism. In the event of light actuation, the tissue to be coagulated is merely clamped and held firmly, but upon forceful closure of the clamping jaws, the tissue parts held between the clamping jaws are additionally severed.

In a first preferred embodiment provision is made for both the cutting element and the clamping elements to be constructed integrally with the clamping jaw, and for the cutting element to be a rigid part of the clamping jaw, while the clamping elements are joined to the remaining parts of the clamping jaw via elastically deformable areas. In particular, the elastically deformable areas can be formed by elastically bendable webs of low height.

In another embodiment provision is made for the clamping jaw to be of two-part construction, with a first rigid part comprising the cutting element and the bearing of the clamping jaw on the grasping instrument, and with a second part comprising the clamping elements and being elastically movably mounted on the first part.

The clamping elements may, for example, be elastically pivotably mounted on the first part.

It is advantageous for the second part to be of U-shaped design with two parallel legs forming the clamping elements and a web joining these legs and closing off the longitudinal slot towards the distal end of the clamping jaw, and for the second part to be rotatably mounted at the free ends of the legs on the first part. This results in a very stable arrangement of the second part of the clamping jaw carrying the clamping surfaces.

The longitudinal slot in the other clamping jaw, which does not have any cutting device, is preferably closed at both ends thereof, so that the cutting device enters this longitudinal slot closed on all sides during the cutting procedure, and this also contributes towards the other clamping jaw forming a very stable arrangement.

The following description of preferred embodiments of the invention serves in conjunction with the drawings to explain the invention in further detail.

DETAILED DESCRIPTION OF THE INVENTION

Figure 1:
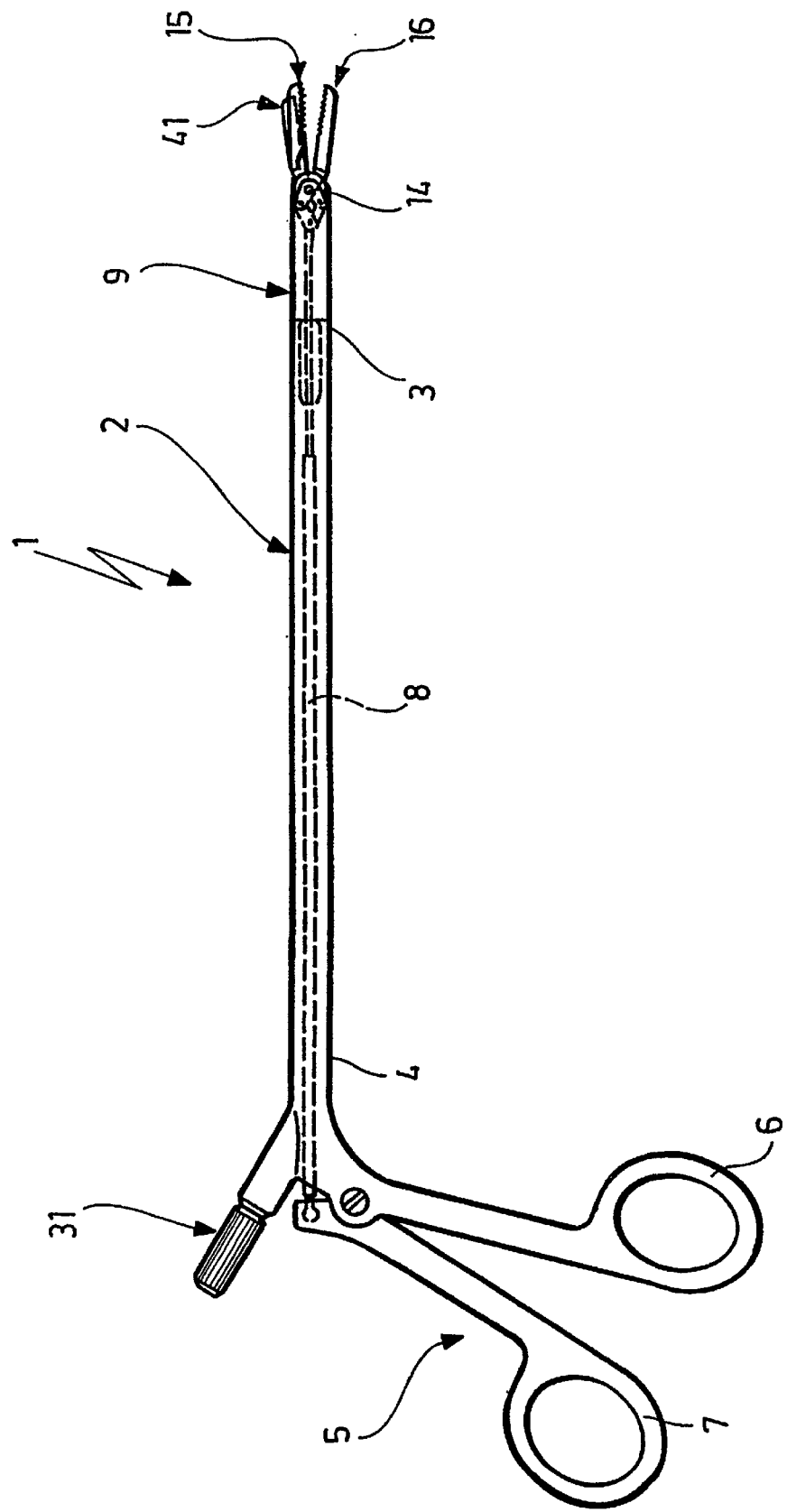
FIG. 1 is a side view of a bipolar grasping instrument designed as a tubular-shafted instrument with two pivotable clamping jaws.
Figure 2:
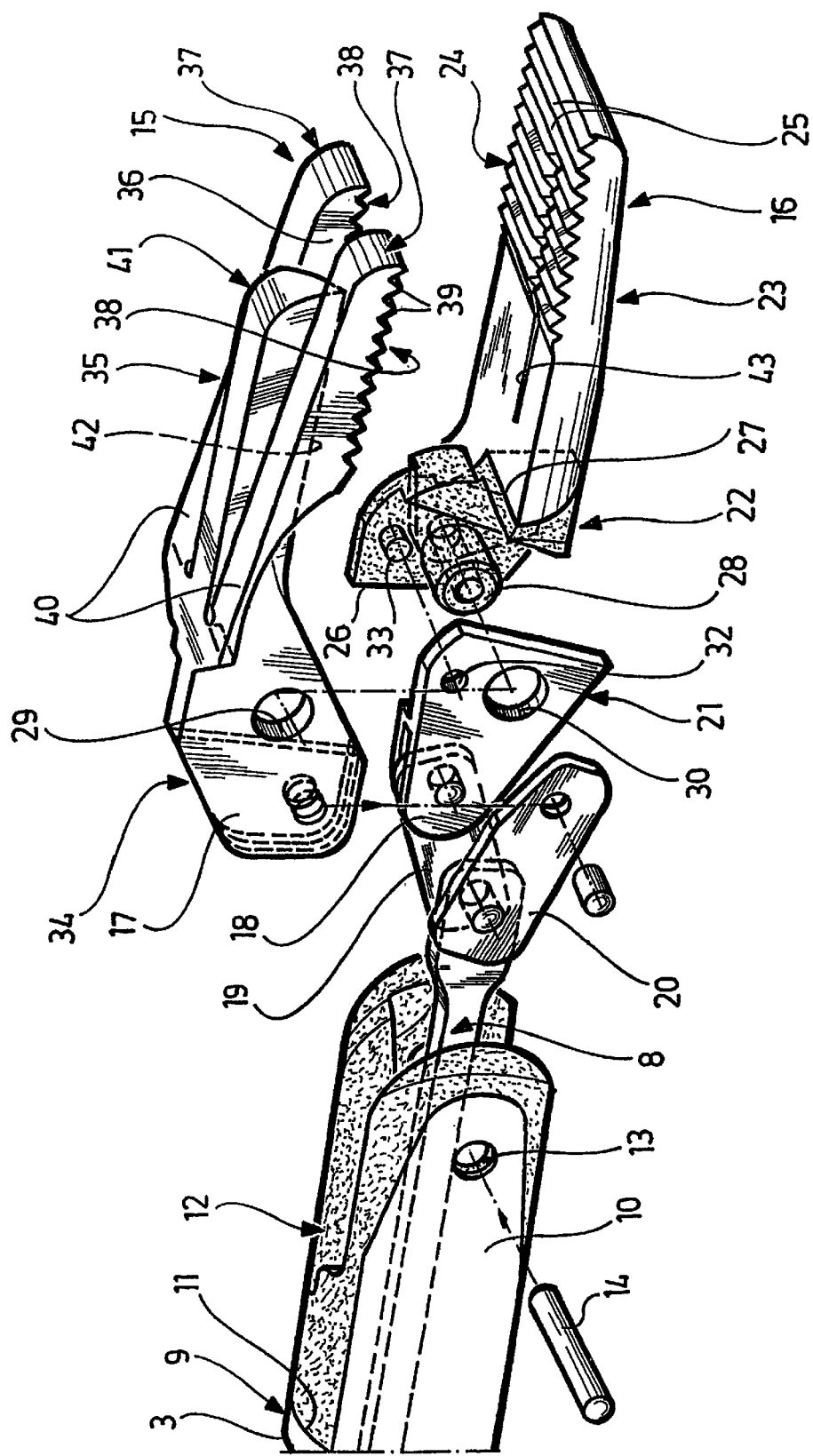
FIG. 2 is a perspective exploded illustration of the two clamping jaws and the drive elements for the clamping jaws.

The surgical instrument shown in the drawings is designed as a tubular-shafted instrument 1, with an elongate, tubular shaft 2 having a distal end 3 and a proximal end 4.

At the proximal end 4, the shaft 2 is connected to a handle 5 comprising a stationary grip 6 and a grip 7 pivotably connected to the grip 6. The grip 7 is articulatedly connected to a push-pull rod 8 which extends through the shaft 2 and is advanceable and retractable in a longitudinal direction by pivoting the grip 7 relative to the shaft 2.

Inserted into the shaft 2 at the distal end 3 thereof is a holder 9 which carries at its distal end two bearing arms 10 extending parallel to one another, projecting in a distal direction and enclosing between them a bearing space 11. Inserted into this bearing space is an insulator 12 made of an electrically insulating material, for example, a ceramic material, which is of substantially U-shaped design and covers the bearing arms 10 on the inside thereof.

The push-pull rod 8 extends through both the holder 9 and the insulator 12 and ends in the area of the bearing space 11.

In the area of their free ends, the bearing arms 10 have openings 13 in alignment with one another for receiving a bearing shaft 14 which extends transversely to the longitudinal direction of the longitudinal axis of the shaft of the instrument and penetrates the bearing space 11 at its distal, open end.

Mounted adjacent to one another on this bearing shaft 14 for pivotal movement independently of one another are two clamping jaws 15, 16, whose proximal ends 17, 18 project into the bearing space 11. Each proximal end 17, 18 is articulatedly connected to a link 19 and 20, respectively, whose other ends are likewise articulatedly connected to the distal end of the push-pull rod 8 so that these links 19, 20 form together with the proximal ends 17 and 18 a four-part linkage via which the clamping jaws 15 and 16 are pivotable about the axis of rotation formed by the bearing shaft 14 upon advancing and retracting the push-pull rod 8: when the push-pull rod 8 is advanced the clamping jaws are pivoted apart, i.e., opened, and when the push-pull rod 8 is retracted the clamping jaws 15, 16 are closed.

The clamping jaws 15 and 16 are of different design. One of the two clamping jaws, referred to hereinbelow as the bottom clamping jaw 16, is of three-part design. It comprises a proximal section 21 extending as far as immediately before the bearing shaft 14, a middle section 22 located substantially in the area of the bearing shaft 14, and a distal section 23 whose substantially flat upper side 24 facing the other clamping jaw 15 forms a clamping surface which is provided with transverse ribs 25 to increase the gripping capability.

The middle section 22 consists of an electrically insulating material, for example, a ceramic material, and connects the proximal section 21 to the distal section 23, thereby electrically insulating these two sections, which consist of metal and are, therefore, electrically conductive. The middle section 22 rests with its surface against both the distal section 23 and the proximal section 21, thereby creating a layered structure in the overlapping area. In addition, the middle section 22 is supported via its rear edge 26 and via a front bearing surface 27 on the proximal section 21 and on the distal section 23, respectively, so that the proximal section 21 is thereby rigidly connected to and electrically isolated from the distal section 23.

At its side, the middle section 22 carries a sleeve 28 which is integrally formed thereon. The sleeve 28 extends through the bearing openings 29 and 30 in the two clamping jaws 15 and 16 and receives the bearing shaft 14 within it. The bearing shaft 14 is thereby electrically isolated from the clamping jaw 15 and the proximal end 18 of the clamping jaw 16. The bearing shaft 14 itself consists of metal and is electrically conductively connected to the bearing arms 10 of the holder 9, which, in turn, is electrically conductively connected to the shaft 2. The shaft 2 carries an electric connection means 31 for establishing an electric connection with a high-frequency voltage source which is not shown in the drawings.

The bearing shaft 14 is in direct contact with the distal section 23 of the clamping jaw 16, so that an electrically conductive connection is established in this area between the distal section 23 and the bearing shaft 14. The distal section 23 of the clamping jaw 16 can thereby be connected to a pole of the high-frequency voltage source.

The other pole is connected in a manner not shown in the drawings to the push-pull rod 8, so that both the proximal section 21 of the clamping jaw 16 and the entire clamping jaw 15 can thereby be connected to this second pole of the high-frequency voltage source via the links 19 and 20.

The middle section 22, which is additionally fixed with respect to the proximal section 21 via a pin 33 engaging a bore 32 of the proximal section 21, separates the distal section 23 of the clamping jaw 16 electrically from the proximal section 21 of the clamping jaw 16 so that the two clamping jaws 15 and 16 are electrically isolated from one another and are each connected to a pole of the voltage source.

The other clamping jaw, referred to hereinbelow as top clamping jaw 15, consists in its entirety of metal and is of integral construction in the embodiment of FIGS. 1 to 4. A proximal section 34 is of similar design to the proximal section 21 of the bottom clamping jaw 16. It passes over into a distal section 35 comprising two clamping elements 37 of identical design which extend parallel to each other and form between them a longitudinal slot 36. Both clamping elements 37 have on their side facing the bottom clamping jaw 16 one clamping surface 38 each, which faces the clamping surface 24 of the bottom clamping jaw 16 and like it is provided with transverse ribs 39.

Both clamping elements 37 are connected to the proximal section 34 via band-shaped webs 40 of low constructional height, which are of such flat design that an elastic pivoting of the arm-like clamping elements 37 is possible in this area, namely about a pivot axis extending parallel to the bearing shaft 14.

Projecting into the longitudinal slot 36 remaining free between the two clamping elements 37 is a cutter 41 which is rigidly connected to the proximal section 34 and whose bottom edge is designed as a cutting edge 42. When the clamping elements 37 are undeformed, i.e., when they are not pivoted elastically with respect to the proximal section 34, the cutting edge 42 is located completely within the longitudinal slot 36, i.e., it does not protrude downwards beyond the clamping surfaces 38 of the two clamping elements 37 (illustration of FIGS. 2 and 3).

However, when the clamping elements 37 are pivoted elastically upwards, i.e., in the opening direction of the clamping jaws, this cutting edge 42 then moves out downwards from between the clamping surfaces 38 and can become operative.

Likewise formed in the bottom clamping jaw 16 is a longitudinal slot 43 which is in alignment with the longitudinal slot 36 in the top clamping jaw 15 and is closed at both ends thereof. The length of the longitudinal slot 43 is of such dimensions that the cutting edge 42 of the cutter 41 can enter the longitudinal slot 43.

The instrument constructed in this way serves in like manner as bipolar grasping instrument and as cutting instrument.

Figures 3, 4:
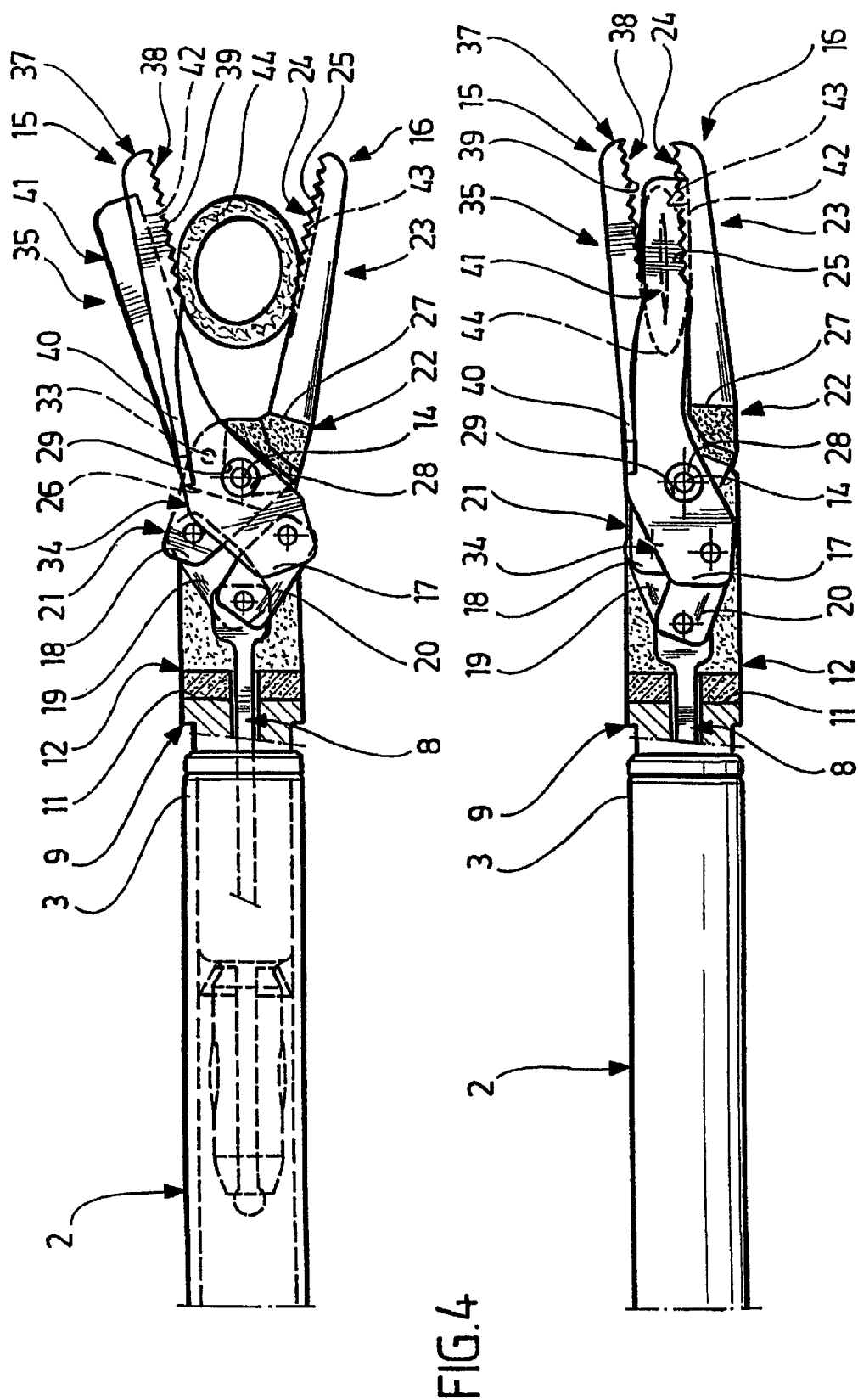
FIG. 3 is a side view of the instrument of FIG. 1 in the clamping jaw area with the clamping jaws in a grasping position.
FIG. 4 is a view similar to FIG. 3 with the clamping jaws in a cutting position.

When the push-pull rod 8 is in the advanced position, the clamping jaws 15 and 16 are first pivoted apart and the forceps are located in the open position. In this position, tissue to be treated, for example, a vessel 44, can be placed against the clamping surfaces 24 and 38 of the clamping jaws and grasped (FIG. 3). In this way, owing to the vessel resting against the two clamping jaws 15 and 16, coagulation of the vessel 44 is possible in the area of contact by applying a high-frequency voltage to the two clamping jaws 15 and 16, as is known per se with bipolar forceps.

This coagulation occurs in a position of the clamping jaws 15, 16 in which these are pivoted into an intermediate position with respect to the open position, but are not yet completely closed. In this intermediate position, the pressure of the top clamping jaw 15 on the vessel 44 is still so low that the clamping elements 37 are not elastically pivoted in the area of the webs 40, but remain undeformed, so that the cutter 41 with the cutting edge 42 remains within the longitudinal slot 36, i.e., the cutting edge 42 is inoperative (FIG. 3).

Upon closing the clamping jaws 15 and 16 further by retracting the push-pull rod 8, however, the clamping jaws 15 and 16 are pressed forcefully against each other, and this causes the clamping elements 37 to be bent in the area of the thin, elastically bendable webs 40, i.e., the clamping elements 37 pivot upwards in the direction opposite to the closed position, and the cutting edge 42 of the cutter 41 can thereby move out downwards beyond the clamping surfaces 38, come to rest against the vessel 44 and sever it upon further closure of the clamping jaws 15 and 16, with the cutter 41 entering with the cutting edge 42 the longitudinal slot 43 of the clamping jaw 16.

Thus, with the same closing movement of the pivotable grip 7, the operator can first grip, then by applying a high-frequency voltage coagulate, and, finally, by further pivoting of the grip 7 transect in the coagulated area the tissue that is to be treated and severed. Only one drive mechanism is required for this, and the operator can carry out this procedure with a single lever which he pivots in accordance with the requirements so that the above-described working positions are assumed one after the other.

Figure 5:
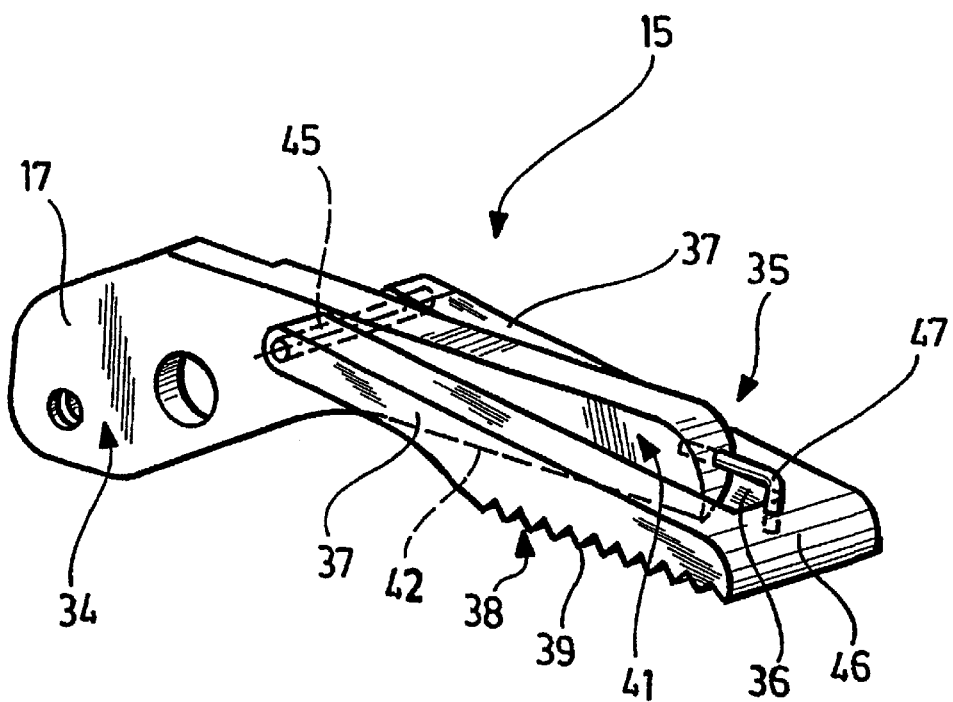
FIG. 5 is a perspective illustration of the clamping jaw provided with a cutting device similar to the illustration of FIG. 2 in a modified embodiment of this clamping jaw.

The embodiment of FIG. 5 is of similar design to that of FIGS. 1 to 4. Like parts are therefore identified by the same reference numerals.

One difference resides solely in the area of the top clamping jaw 15, which in the embodiment of FIG. 5 is of two-part design. In this embodiment, the two clamping elements 37 are not joined to the proximal section 34 of the clamping jaw 15 via elastic webs 40, but are pivotably mounted on the cutter 41 via a bearing pin 45, namely in the area of transition from the cutter 41 to the proximal section 34. At the distal ends, in this embodiment, the clamping elements 37 are joined to one another by a transverse web 46, so that the two clamping elements 37 form together with the transverse web 46 an integral component.

A spring element 47 shown only schematically in the drawing, which is connected, on the one hand, to the cutter 41 and, on the other hand, to the transverse web 46, holds the clamping elements 37 in a position in which the clamping surfaces 38 protrude downwards beyond the cutting edge 42 of the cutter 41, i.e., the cutting edge 42 is fully accommodated in the longitudinal slot 36 and is therefore inoperative. The clamping elements can be elastically pivoted against the action of this spring element 47 so that the cutting edge 42 emerges from the longitudinal slot 36 and becomes operative in the described manner.

In this embodiment, the clamping elements 37 are electrically conductively connected to the proximal section 34 via the bearing pin 45 so that in this case, too, the clamping surfaces 38 are connected to a pole of the high-frequency voltage source.

What is claimed is:

1. Bipolar grasping instrument with two clamping jaws movable relative to each other, electrically isolated from one another and each connectable to a pole of an electric high-frequency voltage source, each of said clamping jaws comprising two clamping elements arranged in spaced relation to one another, forming between them a longitudinal slot and each having a clamping surface, and with a cutting device comprising a cutting element displaceable in the longitudinal slots of the clamping jaws and having a cutting edge, wherein the cutting element is arranged in the longitudinal slot of the one clamping jaw such that its cutting edge is contained in the longitudinal slot between the clamping elements of this clamping jaw and does not extend beyond its clamping surfaces in the direction towards the other clamping jaw, and the clamping elements of this clamping jaw are elastically movable relative to the cutting element opposite to the closing movement of the clamping jaws so far that the cutting edge of the cutting element projects beyond the clamping surfaces.

2. Instrument in accordance with claim 1, wherein both the cutting element and the clamping elements are constructed integrally with the clamping jaw, and the cutting element is a rigid part of the clamping jaw, whereas the clamping elements are joined to the remaining parts of the clamping jaw via elastically deformable areas.

3. Instrument in accordance with claim 2, wherein the elastically deformable areas are formed by elastically bendable webs of low height.

4. Instrument in accordance with claim 2, wherein the longitudinal slot in the other clamping jaw which does not have any cutting device is closed at both ends thereof.

5. Instrument in accordance with claim 1, wherein the clamping jaw is of two-part construction with a rigid first part comprising the cutting element and the bearing of the clamping jaw on the grasping instrument, and with a second part comprising the clamping elements and being elastically movably mounted on the first part.

6. Instrument in accordance with claim 5, wherein the clamping elements are elastically pivotably mounted on the first part.

7. Instrument in accordance with claim 6, wherein the second part is of U-shaped design with two parallel legs forming the clamping elements and a web connecting these legs and closing off the longitudinal slot towards the distal end of the clamping jaw, and the second part is rotatably mounted at the free ends of the legs on the first part.

8. Instrument in accordance with claim 7, wherein the longitudinal slot in the other clamping jaw which does not have any cutting device is closed at both ends thereof.

9. Instrument in accordance with claim 5, wherein the longitudinal slot in the other clamping jaw which does not have any cutting device is closed at both ends thereof.

10. Instrument in accordance with claim 1, wherein the longitudinal slot in the other clamping jaw which does not have any cutting device is closed at both ends thereof.

* * * * *